United States Patent
Onishi et al.

(10) Patent No.: US 7,749,389 B2
(45) Date of Patent: Jul. 6, 2010

(54) FILLER USED FOR SEPARATING OPTICAL ISOMERS AND PROCESS FOR SEPARATING OPTICAL ISOMERS WITH THE FILLER

(75) Inventors: Atsushi Onishi, Ibaraki (JP); Koichi Murazumi, Hyogo (JP); Kozo Tachibana, Ibaraki (JP)

(73) Assignee: Daicel Chemical Industries, Ltd., Osaka (JP)

( * ) Notice: Subject to any disclaimer, the term of this patent is extended or adjusted under 35 U.S.C. 154(b) by 849 days.

(21) Appl. No.: 11/637,157

(22) Filed: Dec. 12, 2006

(65) Prior Publication Data

US 2007/0084796 A1 Apr. 19, 2007

Related U.S. Application Data

(62) Division of application No. 10/398,937, filed as application No. PCT/JP01/09008 on Oct. 12, 2001, now Pat. No. 7,399,409.

(30) Foreign Application Priority Data

Oct. 13, 2000 (JP) .............................. 2000-314244
Jan. 31, 2001 (JP) .............................. 2001-24944

(51) Int. Cl.
*B01D 15/08* (2006.01)
(52) U.S. Cl. ................ 210/659; 210/635; 210/656; 210/198.2
(58) Field of Classification Search ................ 210/635, 210/656, 659, 198.2, 502.1; 502/404
See application file for complete search history.

(56) References Cited

U.S. PATENT DOCUMENTS

| 4,694,044 A | 9/1987 | Kiniwa |
| 4,714,555 A | 12/1987 | Shibata et al. |
| 4,786,415 A | 11/1988 | Shibata et al. |
| 4,786,416 A | 11/1988 | Yuki et al. |
| 4,818,394 A | 4/1989 | Okamoto et al. |
| 5,126,055 A | 6/1992 | Yamashita et al. |
| 5,348,656 A | 9/1994 | Podszun et al. |
| 5,434,298 A | 7/1995 | Negawa et al. |
| 5,770,088 A | 6/1998 | Ikeda et al. |

(Continued)

FOREIGN PATENT DOCUMENTS

EP 154343 A1 9/1985

(Continued)

OTHER PUBLICATIONS

Yashima, E. et al.; Chirality, No. 8, pp. 446-451 (1996).

(Continued)

*Primary Examiner*—Ernest G Therkorn
(74) *Attorney, Agent, or Firm*—Birch, Stewart, Kolasch & Birch, LLP

(57) ABSTRACT

The objectives of this invention are to provide a filler for separating optical isomers, capable of efficiently carrying out optical resolution of optical isomer mixtures, and to provide a process for separating optical isomers by a simulated moving bed chromatography utilizing the filler. This invention provides a filler made of a carrier supporting a specific amount of an optically active high molecular weight compound. Separation by the simulated moving bed chromatography using the filler is carried out under the condition that the capacity factors have specific values.

9 Claims, 7 Drawing Sheets

U.S. PATENT DOCUMENTS

| | | | |
|---|---|---|---|
| 5,772,876 A | | 6/1998 | Murakami |
| 6,130,353 A | | 10/2000 | Bopp |
| 6,946,557 B2 * | | 9/2005 | Onishi et al. ............ 546/173 |

FOREIGN PATENT DOCUMENTS

| | | | |
|---|---|---|---|
| EP | 4710820 | A1 | 2/1992 |
| JP | 62-030549 | A | 2/1987 |
| JP | 62-038238 | A | 2/1987 |
| JP | 04-059047 | A | 2/1992 |
| JP | 4-211021 | A | 8/1992 |
| JP | 05-322866 | A | 12/1993 |
| JP | 06-058920 | A | 3/1994 |
| JP | 6-239767 | A | 8/1994 |
| JP | 06-322001 | A | 11/1994 |
| JP | 07-330802 | A | 12/1995 |

OTHER PUBLICATIONS

Nario Makino, Pharm. Tech. Jpn., vol. 12, No. 1, pp. 43-52, 1996.
O. Ludemann-Hombourger, Sep. Sci. Technol., vol. 35, No. 9, pp. 1285-1305, 2000.
Nario Makino, Kagaku Kogaku, vol. 61, No. 8, pp. 622-625, 2000.
Atsushi Ohnishi, Yuki Gosei Kagaku Kyoukaishi, vol. 54, No. 5, pp. 344-353, 1996.
PTO 05-2810, Translation of Japan Patent No. 62-30549, Apr. 2005.
PTO 05-2843, Translation of Japan Patent No. 04-059047, Apr. 2005.
PTO 05-2811, Translation of Japan Patent No. 62-38238, Apr. 2005.
Abstract of Japan Patent No. 4-211021 (Aug. 3, 1992).
Abstract of Japan Patent No. 6-239767 (Aug. 30, 1994).
Tsunehiko Kurata, Mitsubishi Kasei R&D Review, vol. 6, No. 2, pp. 102-105, 1992.

* cited by examiner

FILLER USED FOR SEPARATING OPTICAL ISOMERS AND PROCESS FOR SEPARATING OPTICAL ISOMERS WITH THE FILLER

This application is a divisional of application Ser. No. 10/398,937, filed Nov. 7, 2003, now U.S. Pat. No. 7,399,409, which in turn is the U.S. national phase under 35 U.S.C. §371 of PCT/JP01/09008, filed Oct. 12, 2001. The entire contents of Ser. No. 10/398,937 and of PCT/JP01/09008 are expressly incorporated by reference in the present application.

TECHNICAL FIELD

This invention relates to a filler used for separating optical isomers and a process for separating optical isomers with the filler. More specifically, this invention relates to a filler suitable for separating a mixture of optical isomers and therefore useful for separating optical isomers. This invention also involves a process for separating optical isomers by a simulated moving bed chromatography using the filler.

BACKGROUND ART

Conventionally, chromatography, especially liquid chromatography, has widely been used as an industrial method of isolating a desired component from an isomer mixture containing two or more components.

This method employs an adsorbent such as an ion-exchanging resin, a zeolite, or a silica gel for the filler, and divides a mixture into components by utilizing the difference in adsorptive properties between the components. For the eluent, water, an organic solvent, or a mixture thereof is used. Concentrating the eluted solution that includes a desired component yields the desired component in a high purity.

The liquid chromatography includes batch methods and simulated moving bed methods, both of which are known to the skilled artisan.

The batch-wise liquid chromatography in an industrial scale can reproduce the results of a chromatography in an analytical scale by similarly scaling up the latter to the former. Therefore a desired component can be obtained in a short time. However, because the amount of the used eluent is large and the adsorbent is not used efficiently, the chromatographic production by the batch-wise liquid chromatography generally costs much. On the other hand, because the simulated moving bed method requires a smaller amount of the eluent than the batch-wise method and it can provide a continuous separation of the components, the productivity is higher than the productivity of the batch-wise liquid chromatography. Consequently, the simulated moving bed method is highly appropriate to the division of isomers in an industrial scale.

An example of the applications where the simulated moving bed chromatography is employed for the resolution of optical isomers is, as disclosed in JP-A-4-211021(1992) or JP-A-6-239767(1994), a method in which a polysaccharide derivative supported on silica gel, which is a carrier, is used for the optical resolution filler.

On the other hand, efforts to reduce the operation cost of a simulated moving bed chromatographic apparatus have been made. For example, the inventors of U.S. Pat. No. 5,518,625, who disclose optical resolution by a simulated moving bed chromatographic method, try to reduce the cost by operating the apparatus under the condition of $0.1 < k' < 1.0$. "k'" means the capacity factor. However, the resulting reduction is very small and it cannot be said that this method succeeds in rooting up this problem.

In view of these situations has been strongly desired a filler and a method for separating optical isomers, which are more excellent in productivity.

The present invention was made based on these situations. The objective of this invention is to provide a method for separating optical isomers, which is more excellent in the productivity of a desired component, by a simulated moving bed chromatography employing an optical resolution filler suitable for the resolution of optical isomers.

SUMMARY OF THE INVENTION

The inventors' intensive researches resulted in a discovery of the following conditions, which led to an improved productivity of the optical resolution of optical isomers.

The amount of an optically active high molecular weight compound, which is supported on a carrier and used as a filler for separating optical isomers, must be at least 23 weight %. Commercially available conventional fillers, such as one taught by U.S. Pat. No. 5,518,625, have the supported polysaccharide derivative in an amount of 10-20 weight %.

When optical resolution is carried out by a simulated moving bed chromatography employing the filler, the capacity factor $k1'$ and/or $k2'$ must be at least 1.

In summary, in order to solve the aforementioned problems, this invention provides a filler for separating optical isomers, which filler comprises a carrier and an optically active high molecular weight compound supported on the carrier, wherein the amount of the optically active high molecular weight compound is at least 23 weight % based on the total weight of the filler.

In a preferred embodiment of the invention relating to the filler, the filler is a polysaccharide derivative.

In a further preferred embodiment of the invention relating to the filler, the polysaccharide derivative is at least one selected from the group consisting of a cellulose ester derivative, a cellulose carbamate derivative, an amylose ester derivative and an amylose carbamate derivative.

In a preferred embodiment of the invention relating to the filler, the average particle size of the carrier is 5-70 μm.

In another preferred embodiment of the invention, the filler for separating optical isomers is used for optical resolution by a simulated moving bed chromatography.

This invention also provides a process for separating optical isomers by a simulated moving bed chromatography that employs a filler for optical resolution, which filler comprises a carrier and an optically active high molecular weight compound supported on the carrier, wherein the amount of the optically active high molecular weight compound is at least 23 weight % based on the total weight if the filler.

In a preferred embodiment relating to the process, the optical resolution is carried out under the conditions that the capacity factors $k1'$ and/or $k2'$, calculated by the following formulae (1) and (2), is at least 1.

$$k1' = (v1 - v0)/v0 \tag{1}$$

$$k2' = (v2 - v0)/v0 \tag{2}$$

wherein each of v1 and v2 is the retention volume of each optical isomer, which is a solute, and v0 is a dead volume.

In a preferred embodiment of the process, the optically active high molecular weight polymer is a polysaccharide derivative.

In a further preferred embodiment relating to the process, the polysaccharide derivative is at least one selected from the group consisting of a cellulose ester derivative, a cellulose carbamate derivative, an amylose ester derivative and an amylose carbamate derivative.

In a preferred embodiment relating to the process, the average particle size of the carrier is 5-70 µm.

DETAILED DESCRIPTION OF THE INVENTION

Figure 1:
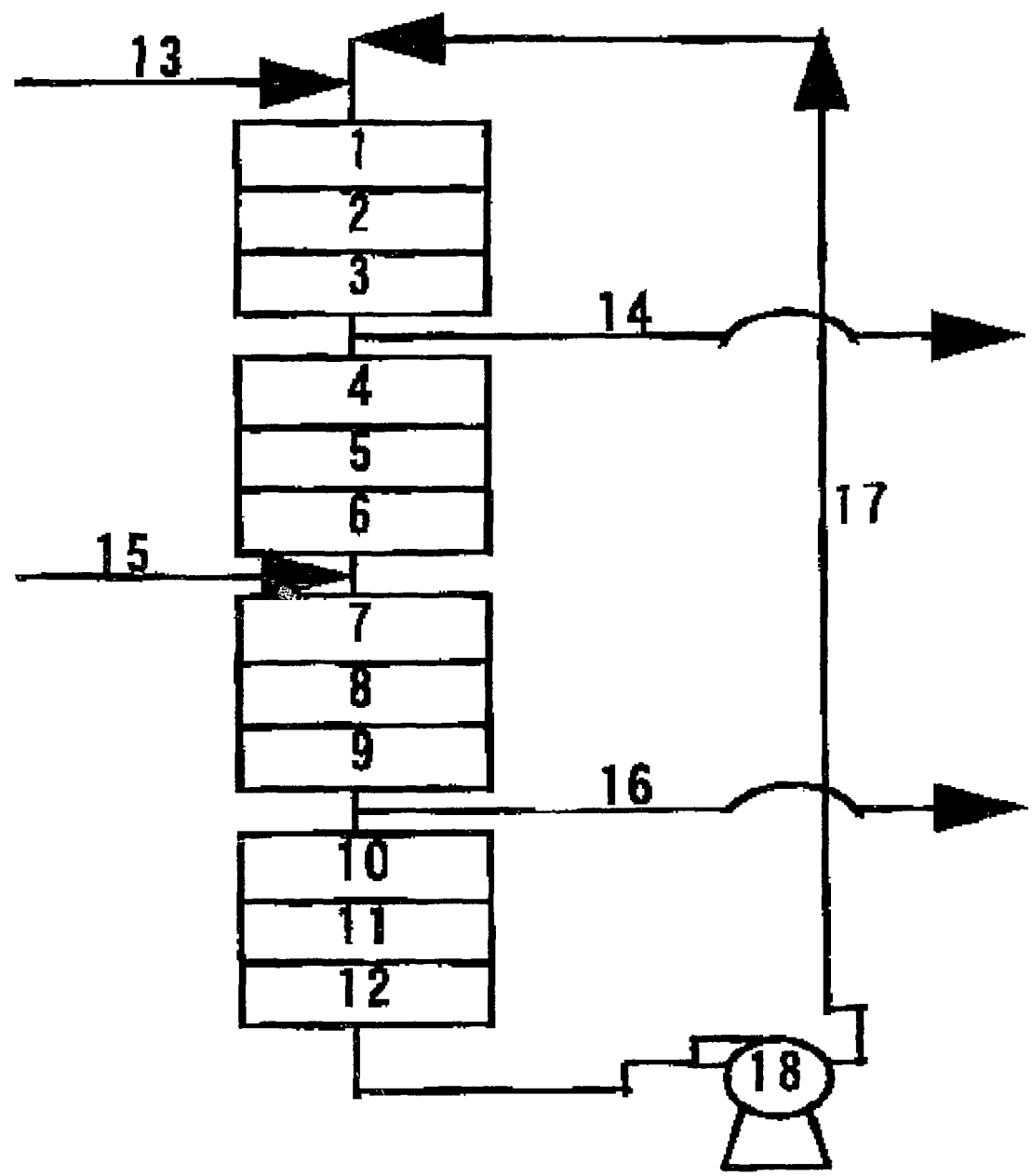
FIG. 1 is a schematic illustration that shows an example of a simulated moving bed chromatographic separation apparatus employed in this invention. In this figure, reference numerals 1-12 denote unit columns, reference numeral 13 denotes an eluent supply conduit, reference numeral 14 an extract draw-out conduit, reference numeral 15 an optical isomer-mixture supply conduit, reference numeral 16 a raffinate draw-out conduit, reference numeral 17 a circulation conduit, and reference numeral 18 a circulation pump.

Preferred Embodiments of the invention will be explained in detail in the followings.

The filler for separating optical isomers has at least 23 weight % of the optically active high molecular weight compound supported on the carrier based on the weight of the filler. When the amount is less than 23 weight %, the load is small, which means low efficiency in the separation of optical isomers, and therefore the process is not industrial. From the viewpoint of productivity, the amount of the optically active high molecular weight compound supported on the carrier is preferably 27 weight % or more based on the weight of the filler. The amount has no upper limit. However, when the amount reaches 60 weight %, the number of the plates is lowered, which undesirably results in low efficiency in the optical separation. As mentioned, the amount of the optically active high molecular weight compound is shown by the weight of the compound to that of the filler.

The optically active high molecular weight compound includes a polymer or copolymer of a (meth) acrylic acid ester or a (meth) acrylic amide that does not have optically active substituents, a (meth) acrylic acid ester or a (meth) acrylic amide that has optically active substituents, styrene, acetylene, etc., a polysaccharide and polymers thereof, a peptide, a protein, etc. Preferable are high molecular weight compounds having an ability to identify the asymmetric carbon atom, especially, a polymer or copolymer of a (meth) acrylic acid ester or a (meth) acrylic amide, a polysaccharide and polymers thereof, and proteins, which are known as polymers having an ability to identify the asymmetric carbon. Please note that in this specification "(meth) acrylic acid ester" means "acrylic acid ester" or "methacrylic acid ester", and "(meth) acrylic amide" means "acrylic amide" or "methacrylic amide". Among these polymers preferred are a polymer or copolymer of a (meth) acrylic acid ester or a (meth) acrylic amide, which polymer or copolymer has optically active groups in their side chains, and a polysaccharide and derivatives thereof. A polysaccharide derivative is particularly preferable. The polysaccharide derivative may be any of synthesized polysaccharide, naturally occurring polysaccharide and modified natural polysaccharide, as long as it is optically active.

Specific examples of the polysaccharides are: α-1,4-glucan (amylose, amylopectin), β-1,4-glucan (cellulose), α-1,6-glucan (dextran), β-1,6-glucan (pustulan), α-1,3-glucan, β-1,3-glucan (curdlan, schizophylan, etc.), β-1,2-glucan (Crawn Gall polysaccharide), β-1,4-galactan, α-1,6-mannan, β-1,4-mannan, β-1,2-fructan (inuline), β-2,6-fructan (levan), β-1,4-xylan, β-1,3-xylan, β-1,4-N-acetylchitosan (chitin), pullulan, agalose, arginic acid, cyclodextrins, etc.

Among them preferred are cellulose, amylose, β-1,4-mannan, inuline, curdlan, etc. because highly pure products are available easily. Cellulose, amylose, etc. are particularly preferable.

The number average polymerization degree, which is indicated by an average number of pyranose or furanose rings per molecule, of these polysaccharides is typically at least 5, preferably not less than 10. This degree does not have specific upper limits. In view of ease in handling, however, it should be not more than 1000, preferably not more than 500. Furthermore, the number average polymerization degree ranges preferably between 5 and 1000, more preferably between 10 and 1000, particularly preferably between 10 and 500.

Preferred polysaccharide derivatives include polysaccharide ester derivatives and polysaccharide carbamate derivatives.

Particularly preferred are polysaccharide compounds in which part of or all of the hydrogen atoms on the hydroxy groups or amino groups of the polysaccharide are substituted with at least one of the atomic groups represented by the following chemical formulae (1), (2), (3) and (4):

(1)

(2)

(3)

(4)

wherein R stands for an aromatic group which may contain a hetero atom and may be unsubstituted or substituted with at least one selected from the group consisting of an alkyl group having 1-12 carbon atoms, an alkoxy group having 1-12 carbon atoms, an alkylthio group having 1-12 carbon atoms, cyano group, a halogen atom, an acyl group having 1-8 carbon atoms, an alkoxycarbonyl group having 1-8 carbon atoms, nitro group, amino group and an alkylamino group having 1-8 carbon atoms. The aromatic group includes phenyl, naphthyl, phenanthryl, anthracyl, indenyl, furyl, thionyl, pyryl, benzofuryl, benzothionyl, indyl, pyridyl, pyrimidyl, quinolyl, isoquinolyl, etc. Of these, phenyl, naphthyl, pyridyl, etc. are preferred. Particularly preferred Rs are a halogenated phenyl and an alkyl phenyl.

X stands for a hydrocarbon group having 1-4 carbon atoms, which may contain a double bond or triple bond. Examples of X are methylene, methyl methylene, ethylene, ethylidene, ethenylene, ethynylene, 1,2- or 1,3-propylene, 1,1- or 2,2-propylidine group, etc.

The carbamate derivatives of the polysaccharide desirably usable in the present invention are obtained by reacting an isocyanate represented by the following formula (5) or (6) with the polysaccharide, and the ester derivatives of the polysaccharide desirably usable in the present invention are obtained by reacting an acid chloride represented by the following formula (7) or (8) with the polysaccharide:

(5)

(6)

(7)

(8)

wherein R and X are as defined above.

The degree of substitution with the atomic groups described here in before in the polysaccharide is usually 10%-100%, preferably 30%-100% and more preferably 80%-100%. The degree of less than 10% is not preferable because the resulting polysaccharide has little ability of optical resolution. Also, the degree of less than 30% is not very preferable because optical resolution is sometimes insufficient depending upon the species and concentration of the optical isomer mixture to be separated. On the other hand, the degree in excess of 80% is preferable because particles for the filler having excellent optical resolution ability can be obtained. The degree can be determined by elemental analysis of carbon, hydrogen and nitrogen before and after the substitution.

For the carrier can be used organic and inorganic porous substances. The inorganic porous substances are preferable. Examples of the suitable organic carriers are a high molecular weight compound selected from the group consisting of polystyrene, polyacrylamide, polyacrylate, etc. Examples of the suitable inorganic carriers are silica gel, alumina, magnesia, zirconia, glass, kaolin, titanium oxide, silicate salts, hydroxy apatite, etc. The especially preferable carrier is silica gel. The average particle size of silica gel is usually 5-70 µm, preferably 10-50 µm. When the average particle size is less than 5 µm, the operational pressure of the apparatus is raised. On the other hand, when the average particle size is more than 70 µm, the productivity is lowered, which is also undesirable. The average pore size of silica gel is 10 Å-100 µm, preferably 50 Å-50,000 Å. The surface of the carrier should be treated to remove the remaining silanol that might have undesirable effects on the surface and to improve an affinity for the optically active high molecular weight compound. However, if the surface is not treated at all, it will not cause problems.

Examples of preferable surface treatments are a silane finish with an organic silane compound and a treatment by a plasma polymerization.

The filler for separating optical isomers may be prepared either through a direct bonding of the optical active high molecular weight compound, e.g. a polysaccharide derivative, with the carrier, or through coating the carrier with a solution of the optical active high molecular weight compound and removing the solvent by distillation. The solvent may be any organic solvent that is commonly used, as long as it can dissolve the optical active high molecular weight compound such as a polysaccharide derivative.

Moreover, by forming further chemical bonds between the carrier and the optical active high molecular weight compound such as a polysaccharide derivative, and between the molecules of the optical active high molecular weight compound itself on the carrier, the compound may be firmly fixed on the carrier. The chemical bonds may be formed through reactions by utilizing another component, by irradiating the compound on the carrier with light, radiant rays such as γ ray or electromagnetic waves such as micro wave, or by forming radicals with a free-radical initiator.

The separation method employing the simulated moving bed chromatography in accordance with this invention is suitable for separating optical isomer mixtures. The optical isomer mixtures include ethyl 7-[2-cyclopropyl-4-(4-fluorophenyl) quinolin-3-yl]-3,5-dihydroxy-6-heptenoate. Various optical isomer mixtures other than the above-mentioned, for example, disopyramide and warfarin, may be used for the feedstock. This method may employ, depending on the mixture to be separated, either of a normal phase chromatography where an organic solvent is the mobile phase and a reversed-phase chromatography where an aqueous solvent is the mobile phase. Further, for the separation of optical isomer mixtures may be employed a supercritical fluid chromatography in which the mobile phase is a supercritical fluid.

An example of the simulated moving bed chromatographic separation method will be given in the followings. It should be noted that the separation method in accordance with the invention is not limited to the example and that the conditions including the cycle time may be set at the operator's discretion for optimizing the operation, as disclosed by, e.g. WO 00/25885.

Separation through adsorption of optical isomers by a simulated moving bed chromatography is effected by continuously carrying out an adsorption step, a concentration step, a desorption step and an eluent recovery step in circulation.

(1) Adsorption Step

An optical isomer mixture solution is contacted with a filler, whereby an optically active isomer easily adsorbed by the filler (strongly adsorbable substance) is adsorbed by the filler while the other optical isomer not easily adsorbed by the filler (poorly adsorbable substance) goes into raffinate, which is recovered together with the eluent.

(2) Concentration Step

The filler, which has adsorbed the strongly adsorbable substance, is contacted with a portion of extract as will be described below, the poorly adsorbable substance retained on the filler is expelled, and thus the adsorbable substance is concentrated.

(3) Desorption Step

The filler, which has the concentrated strongly adsorbable substance is contacted with the eluent, and the substance is expelled from the filler and taken out of the simulated moving bed apparatus together with the eluent as extract.

(4) Eluent Recovery Step

The filler that contains substantially only the eluent is contacted with a portion of the raffinate, and a portion of the eluent contained in the filler is recovered as an eluent recovery.

Figure 2:
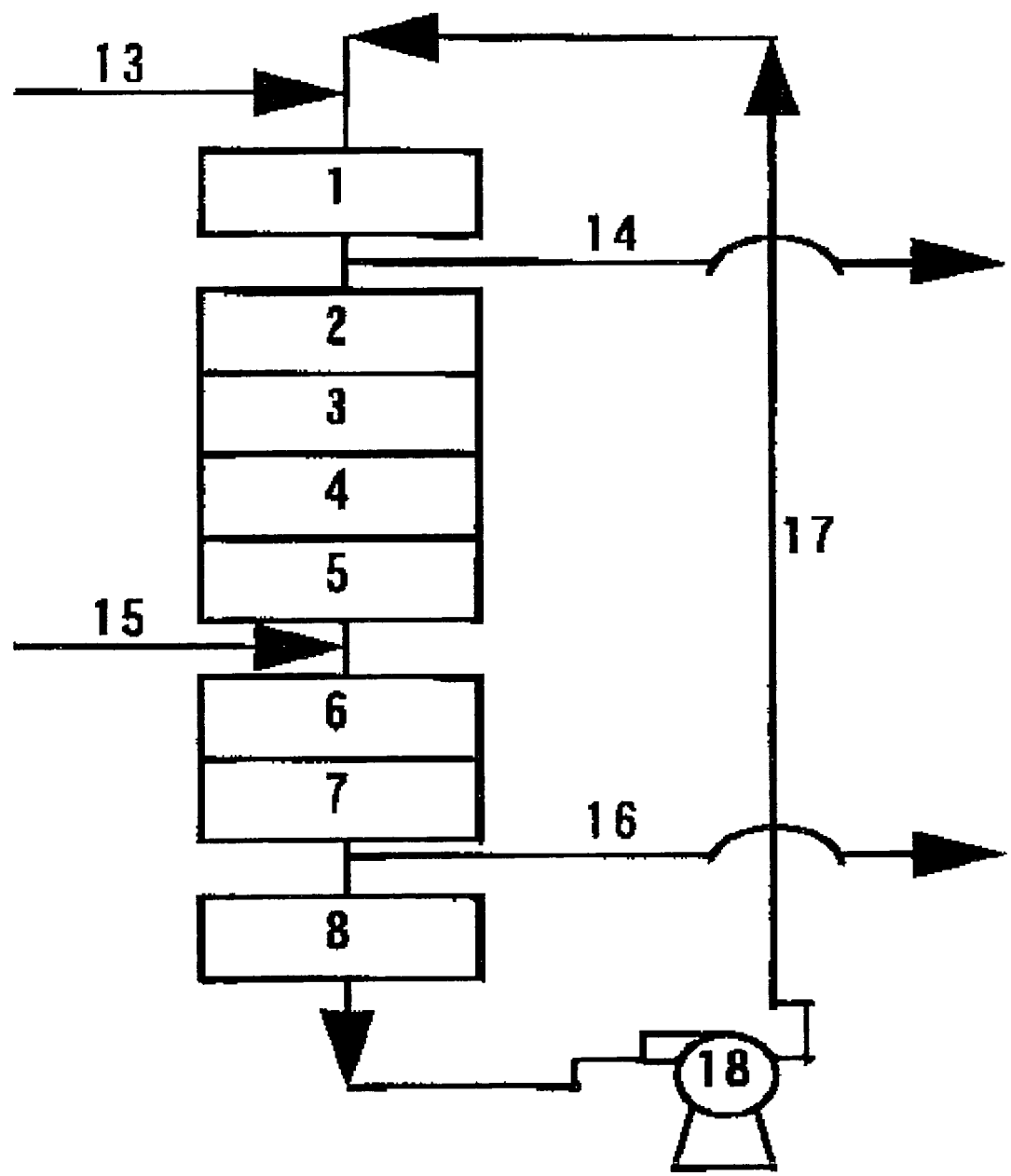
FIG. 2 is a schematic illustration that shows another example of a simulated moving bed chromatographic separation apparatus employed in this invention.

Now the procedures are explained in detail with reference to the attached drawings. FIG. 1 is a schematic illustration that shows an example of a simulated moving bed chromatographic apparatus employed in this invention. FIG. 2 is a schematic illustration that shows another example of a simulated moving bed chromatographic apparatus employed in this invention.

In FIG. 1, the beds, which are the main part of the simulated moving bed chromatographic apparatus, are divided into 12 (twelve) unit columns. In FIG. 2, the apparatus has 8 (eight) unit columns. The number of the unit columns and the size of each unit column are not limited to the above-mentioned, but decided depending on the factors such as the composition and flow rate of the optical isomer mixture solution, and the pressure loss and the dimensions of the apparatus.

In FIG. 1, unit columns 1-12 are filled with a filler and they are mutually connected with fluid passages. The eluent is introduced through eluent supply conduit 13, the extract is taken out through extract conduit 14, the mixture solution containing optical isomers is supplied via conduit 15, the raffinate is taken out through raffinate conduit 16, and the fluid is recirculated through recirculation conduit 17 by means of pump 18.

In the state of unit columns 1-12 and conduits 13-16 as shown in FIG. 1, desorption is done in unit columns 1-3, concentration in unit columns 4-6, adsorption in unit columns 7-9, and eluent recovery in unit columns 10-12. In the simulated moving bed system like this, the working positions of the respective supply conduits and the respective taking-out conduits are shifted one unit column by one unit column in the fluid flow direction at a constant time interval by operation of valves. In the next stage, therefore, desorption is done in unit columns 2-4, concentration in unit columns 5-7, adsorption in unit columns 8-10, and eluent recovery in unit columns 11-1. By repeating this operation successively, each step is carried out in a set of unit columns that are shifted one column by one column. Thus optical resolution of an optical isomer mixture is efficiently achieved.

In the state of unit columns 1-8 and conduits 13-16 as shown in FIG. 2, eluent recovery is done in unit column 1, adsorption in unit columns 2-5, concentration in unit columns 6-7, and desorption in unit column 8. In the simulated moving bed system like this, the working positions of the respective supply conduits and the respective taking-out conduits are shifted one unit column by one unit column in the fluid flow direction at a constant time interval by operation of valves. In the next stage, therefore, desorption is done in unit column 2, concentration in unit columns 3-6, adsorption in unit columns 7-8, and eluent recovery in unit column 1. By repeating this operation successively, each step is carried out in a set of unit columns that are shifted one column by one column. Thus optical resolution of an optical isomer mixture is efficiently achieved.

In the present process employing the simulated moving bed chromatography, the chromatographic separation should be carried out under the condition that capacity factor k' is at least 1 (in other words, capacity factor k' is not less than 1). In this specification "k1'" and "k2'" mean the capacity factors calculated by the following formulae:

$$k1'=(v1-v0)/v0 \quad (1)$$

$$k2'=(v2-v0)/v0 \quad (2)$$

wherein v1 and v2 each are the respective retention volumes of the optical isomers, which are eluted components, and v0 is a dead volume.

When both of capacity factors k1' and k2' are less than 1, the productivity is lowered, which is undesirable. Either of k1' and k2' should be at least 1. From the viewpoint of improving productivity, more preferable is that both of the factors are at least 1.

EXAMPLES

Synthesizing Example 1

Preparation of an HPLC Column Containing a Filler that Includes 24 Weight % of Cellulose Tris(4-chlorophenyl-carbamate)

(1) Surface Treatment of Silica Gel

A porous silica gel (the average particle size: 20 μm) was subjected to an aminopropyl silane treatment (APS treatment) through the reaction of the silica gel with 3-aminopropyl triethoxy silane by a known method. Reaction of the obtained APS-treated silica gel with 3,5-dimethyl phenyl isocyanate produced a carbamoyl-surface-treated silica gel. The content of carbon atoms included in this treated silica gel determined by elemental analysis is shown in Table 1. The content is shown in percentage and abbreviated to "C %".

(2) Synthesis of Cellulose Tris(4-chlorophenyl carbamate)

Under nitrogen atmosphere, 100 g of cellulose and 714.1 g (2.5 equivalent weight) of 4-chlorophenyl carbamate in 3.8 liters of dried pyridine were heated and stirred for 60 hours at the reflux temperature of pyridine. The solution was poured into 40 liters of 2-propanol. The formed precipitate was isolated by filtration with a glass filter, washed several times with 2-propanl, and then vacuum-dried at 80° C. for 15 hours. The collected was a yellowish white solid product, which weighed 287 g. The yield was 75%. The carbon content (C %) of this cellulose tris (4-chlorophenyl carbamate) determined by elemental analysis is shown in Table 1.

(3) Preparation of a Filler made of Silica Gel Supporting 24 Weight % of Cellulose Tris(4-chlorophenyl carbamate)

120 g of cellulose tris (4-chlorophenyl carbamate) obtained in step (2) above was dissolved in 600 ml of acetone. 380 g of the treated silica gel prepared in step (1) above was uniformly coated with the half amount of this polymer solution. The acetone was vacuum-distilled off from the coated silica gel at 40° C. for 45 minutes under 40 kPa. The silica gel was again coated with the remaining half of the polymer solution, and acetone was vacuum-distilled off in the same way. Then, the aimed filler made of silica gel supporting 24 weight % of cellulose tris (4-chlorophenyl carbamate) was obtained. The carbon content (C %) of this filler determined by elemental analysis and the content of the supported cellulose tris(4-chlorophenyl carbamate) in the filler are shown in Table 1.

(4) Preparation of a Filled HPLC Column from the Prepared Filler

A stainless steel column of 25 cm in length and 0.46 cm in inner diameter was filled with the filler made of silica gel supporting cellulose tris(4-chlorophenyl carbamate), which was prepared in step (3) above, by the slurry method. Then a separation column for optical isomers was obtained.

Synthesizing Example 2

Preparation of an HPLC Column Containing a Filler that Includes 30 Weight % of Cellulose Tris(4-chlorophenyl-carbamate)

(1) Surface Treatment of Silica Gel

The surface treatment was carried out in the same way as explained in Synthesizing Example 1 (1).

(2) Synthesis of Cellulose Tris(4-chlorophenyl carbamate)

Cellulose tris(4-chlorophenyl carbamate) was synthesized in the same way as explained in Synthesizing Example 1 (2).

(3) Preparation of a Filler Made of Silica Gel Supporting 30 Weight % of Cellulose Tris(4-chlorophenyl carbamate)

150 g of cellulose tris (4-chlorophenyl carbamate) obtained in step (2) above was dissolved in 800 ml of acetone. 350 g of the treated silica gel prepared in step (1) above was uniformly coated with this polymer solution. The acetone was vacuum-distilled off from the coated silica gel at 40°C. for 30 minutes under 40 kPa. Then, the aimed filler made of silica gel supporting 30 weight % of cellulose tris(4-chlorophenyl carbamate) was obtained. The carbon content (C %) of this filler determined by elemental analysis and the content of the supported cellulose tris(4-chlorophenyl carbamate) in the filler are shown in Table 1.

(4) Preparation of a Filled HPLC Column from the Prepared Filler

A stainless steel column of 25 cm in length and 0.46 cm in inner diameter was filled with the filler made of silica gel supporting cellulose tris(4-chlorophenyl carbamate), which was prepared in step (3) above, by the slurry method. Then a separation column for optical isomers was obtained.

Synthesizing Example 3

Preparation of an HPLC Column Containing a Filler that Includes 20 weight % of Cellulose Tris(4-Chlorophenyl Carbamate)

(1) Surface Treatment of Silica Gel

The surface treatment was carried out in the same way as explained in Synthesizing Example 1 (1).

(2) Synthesis of Cellulose Tris(4-Chlorophenyl Carbamate)

Cellulose tris(4-chlorophenyl carbamate) was synthesized in the same way as explained in Synthesizing Example 1 (2).

(3) Preparation of a Filler made of Silica Gel Supporting 20 Weight % of Cellulose Tris(4-Chlorophenyl Carbamate)

100 g of cellulose tris(4-chlorophenyl carbamate) obtained in step (2) above was dissolved in 600 ml of acetone. 400 g of the treated silica gel prepared in step (1) above was uniformly coated with this polymer solution. The acetone was vacuum-distilled off from the coated silica gel at 40° C. for 30 minutes under 40 kPa. Then, the aimed filler made of silica gel supporting 20 weight % of cellulose tris(4-chlorophenyl carbamate) was obtained. The carbon content (C %) of this filler determined by elemental analysis and the content of the supported cellulose tris(4-chlorophenyl carbamate) in the filler are shown in Table 1.

(4) Preparation of a Filled HPLC Column from the Prepared Filler

A stainless steel column of 25 cm in length and 0.46 cm in inner diameter was filled with the filler made of silica gel supporting cellulose tris(4-chlorophenyl carbamate), which was prepared in step (3) above, by the slurry method. Then a separation column for optical isomers was obtained.

TABLE 1

| | C % | Calculated content of the supported |
|---|---|---|
| S.E.1(1) carbamoyl-treated silica gel | 1.10 | — |
| S.E.1(2) cellulose tris (4-chlorophenyl carbamate) | 51.38 | — |
| S.E.1(3) filler loaded with cellulose tris(4-chlorophenyl carbamate) | 13.21 | 23.9 |

TABLE 1-continued

| | C % | Calculated content of the supported |
|---|---|---|
| S.E.2(3) filler loaded with cellulose tris(4-chlorophenyl carbamate) | 15.79 | 29.2 |
| S.E.3(3) filler loaded with cellulose tris(4-chlorophenyl carbamate) | 11.10 | 19.9 |

The calculation formula for calculating the amount of the supported from the carbon content (C %) determined by the elemental analysis is as follows:

{[C % (filler loaded with cellulose tris (4-chlorophenyl carbamate))-C %(carbamoyl-treated silica gel)]/[C % (cellulose tris(4-chlorophenyl carbamate))-C % (carbamoyl-treated silica gel)]}×100

Working Example 1

Measurement of the Capacity Factors and Simulated Moving Bed Chromatographic Separation using the Column and the Filler Made in Synthesizing Example 1

Figure 3:
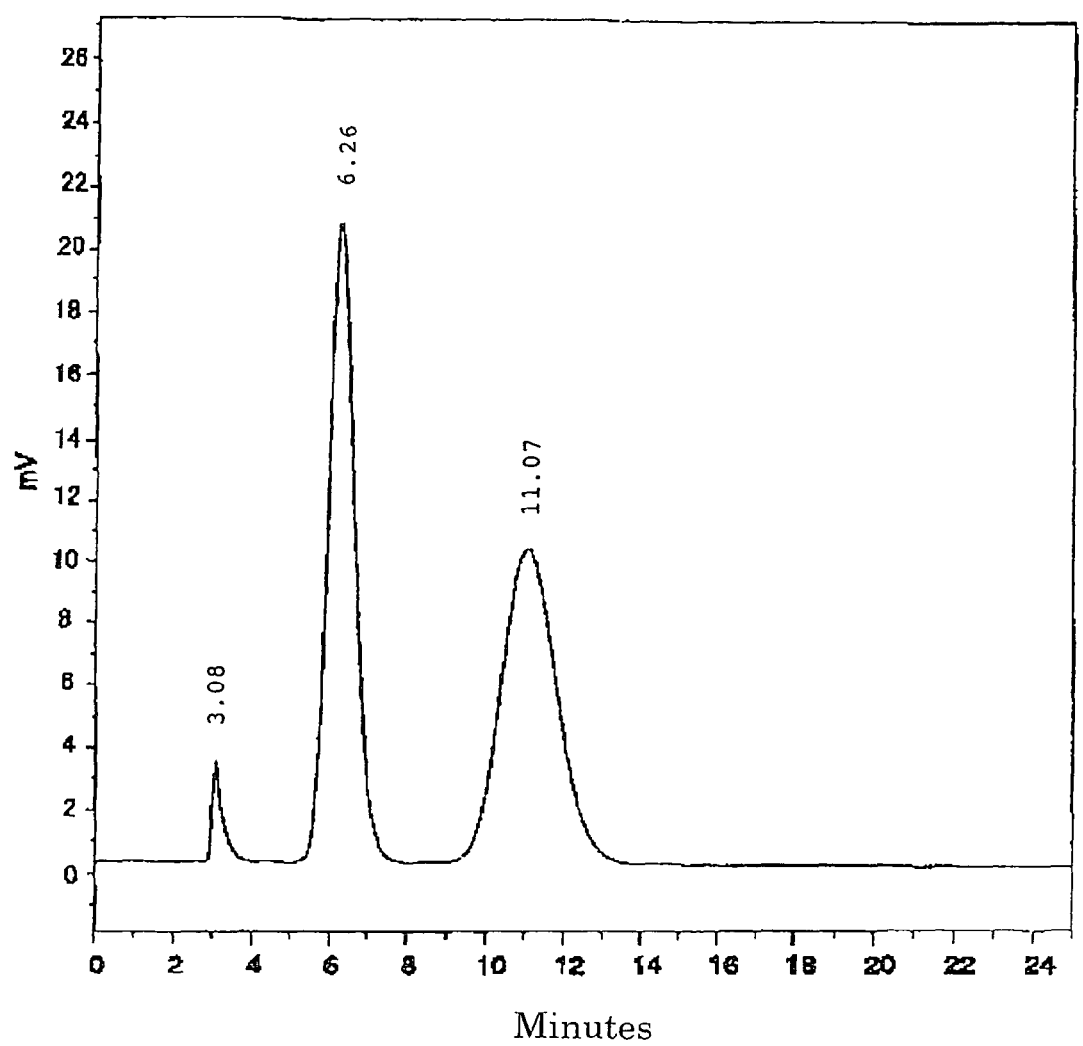
FIG. 3 is a chromatogram obtained in Working Example 1.

Disopyramide represented by formula (9) was analyzed with the HPLC column made in Synthesizing Example 1, which HPLC column was fixed in a liquid chromatographic apparatus. The conditions of the analysis and the capacity factors obtained are shown in Table 2. The chromatogram is shown in FIG. 3.

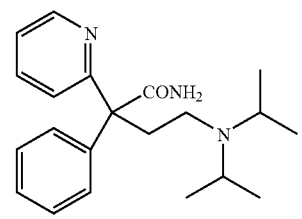

(9)

Eight (8) stainless steel columns, each being 1.0 cm in inner diameter and 10 cm in length, were filled by the slurry method with the filler prepared in Synthesizing Example 1. The columns were fixed to a small-sized simulated moving bed chromatographic separation apparatus and then separation was carried out. The operational conditions are shown below. The respective optical purities of the obtained raffinate and extract, and the productivity of the raffinate are shown in Table 3.

Mobile phase: n-hexane/2-propanol/diethylamine 25/75/0.1 (vol.) mixture

Column temperature: 40° C.

Supply rate of feedstock: 1.79 ml/min.

Flow rate of raffinate: 3.12 ml/min.

Flow rate of extract: 9.63 ml/min.

Flow rate of eluent: 10.96 ml/min.

Step time: 2.5 min.

Concentration of feedstock: 50 mg/ml-mobile phase

Flow rate in zone I: 13.97 ml/min.

Flow rate in zone II: 4.34 ml/min.

Flow rate in zone III: 6.13 ml/min.

Flow rate in zone IV: 3.00 ml/min.

Working Example 2

Measurement of the Capacity Factors and Simulated Moving Bed Chromatographic Separation Using the Column and the Filler Made in Synthesizing Example 2

Figure 4:
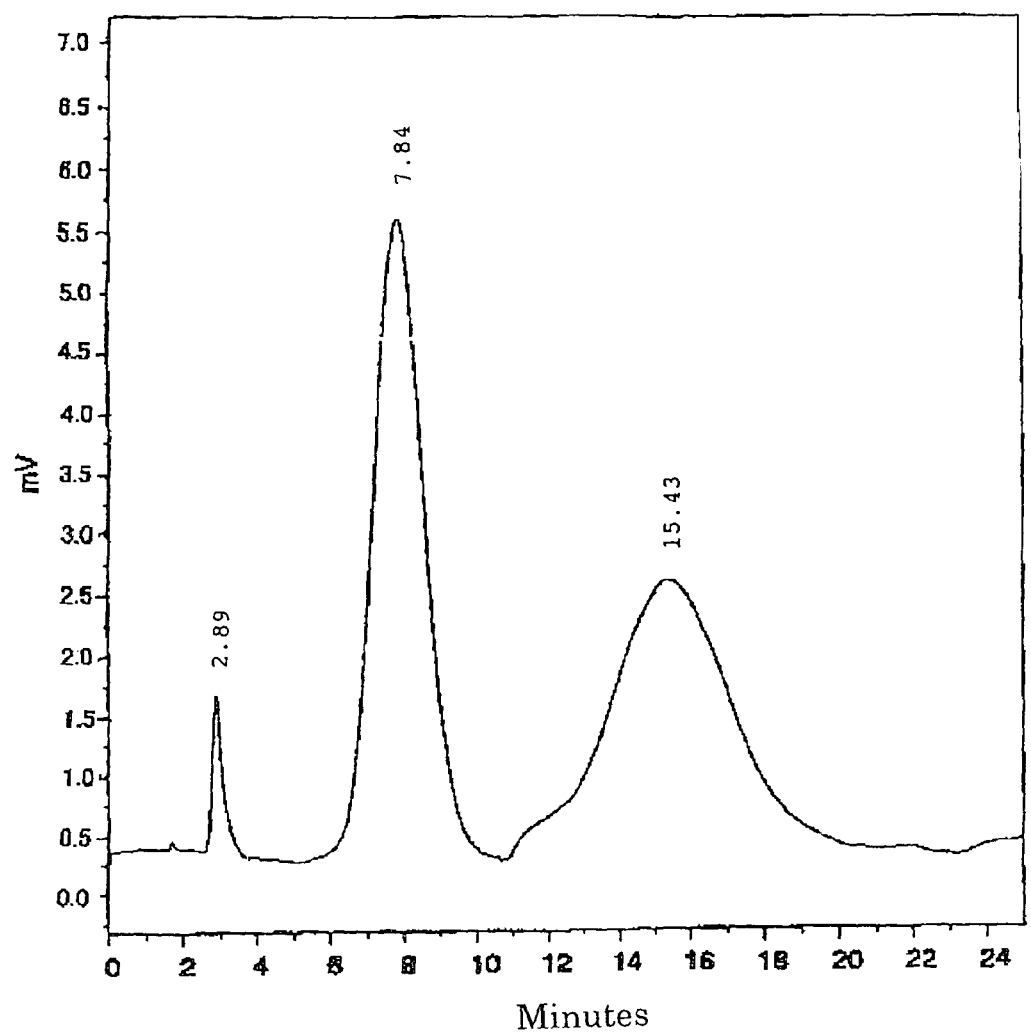
FIG. 4 is a chromatogram obtained in Working Example 2.

Disopyramide represented by formula (9) was analyzed with the HPLC column made in Synthesizing Example 2, which HPLC column was fixed in a liquid chromatographic apparatus. The conditions of the analysis and the capacity factors obtained are shown in Table 2. The chromatogram is shown in FIG. 4.

8 (eight) stainless steel columns, each being 1.0 cm in inner diameter and 10 cm in length, were filled by the slurry method with the filler prepared in Synthesizing Example 2. The columns were fixed to a small-sized simulated moving bed chromatographic separation apparatus and then separation was carried out. The operational conditions are shown below. The respective optical purities of the obtained raffinate and extract, and the productivity of the raffinate are shown in Table 3.

Mobile phase: n-hexane/2-propanol/diethylamine 25/75/0.1 (vol.) mixture
Column temperature: 40° C.
Supply rate of feedstock: 1.83 ml/min.
Flow rate of raffinate: 4.24 ml/min.
Flow rate of extract: 14.55 ml/min.
Flow rate of eluent: 16.96 ml/min.
Step time: 2.5 min.
Concentration of feedstock: 50 mg/ml-mobile phase
Flow rate in zone I: 20.44 ml/min.
Flow rate in zone II: 5.89 ml/min.
Flow rate in zone III: 7.72 ml/min.
Flow rate in zone IV: 3.48 ml/min.

Comparative Example 1

Measurement of the Capacity Factors and Simulated Moving Bed Chromatographic Separation Using the Column and the Filler Made in Synthesizing Example 3

Figure 5:
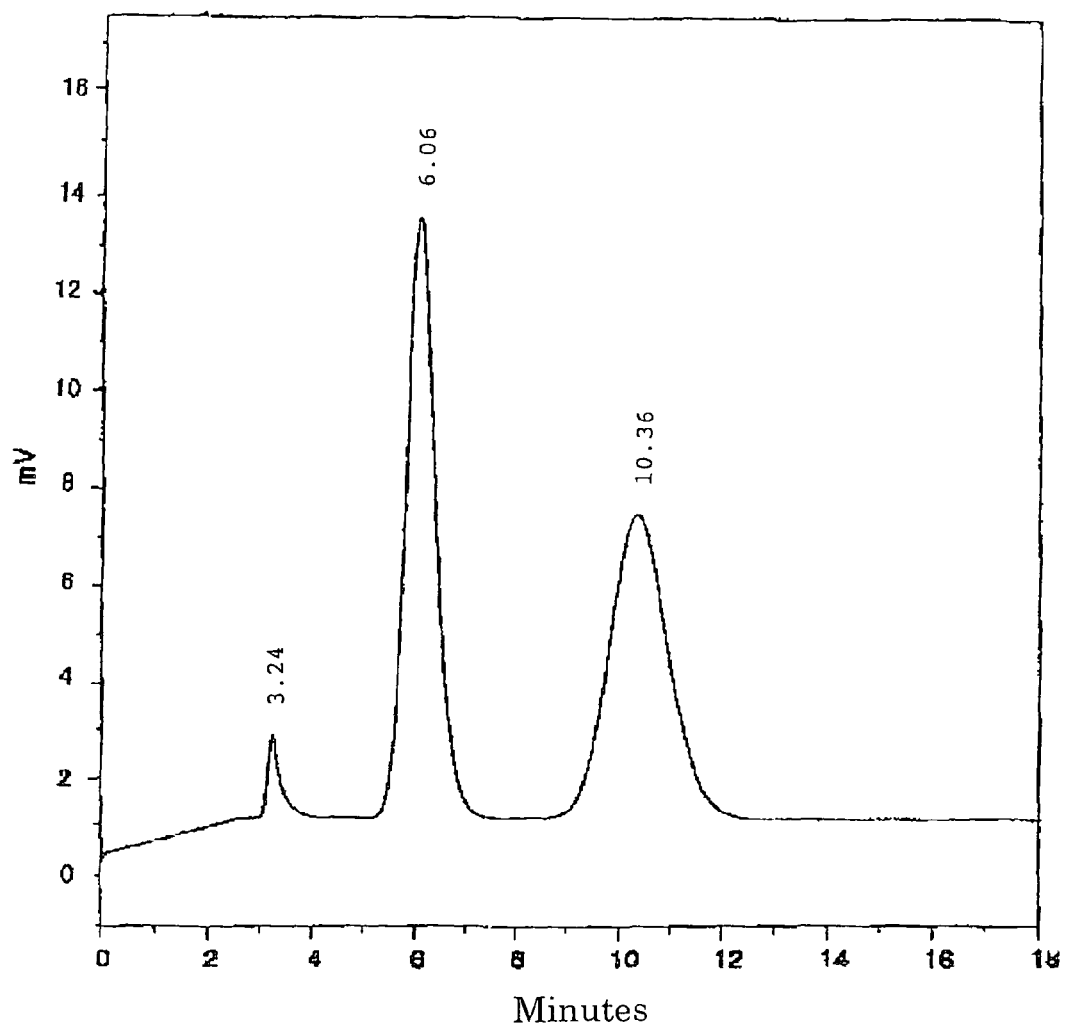
FIG. 5 is a chromatogram obtained in Comparative Example 1.

The compound represented by formula (9) was analyzed with the HPLC column made in Synthesizing Example 3, which HPLC column was fixed in a liquid chromatographic apparatus. The conditions of the analysis and the capacity factors obtained are shown in Table 2. The chromatogram is shown in FIG. 5.

8 (eight) stainless steel columns, each being 1.0 cm in inner diameter and 10 cm in length, were filled by the slurry method with the filler prepared in Synthesizing Example 3. The columns were fixed to a small-sized simulated moving bed chromatographic separation apparatus and then separation was carried out. The operational conditions are shown below. The respective optical purities of the obtained raffinate and extract, and the productivity of the raffinate are shown in Table 3.

Mobile phase: n-hexane/2-propanol/diethylamine 25/75/0.1 (vol.) mixture
Column temperature: 40° C.
Supply rate of feedstock: 1.60 ml/min.
Flow rate of raffinate: 2.90 ml/min.
Flow rate of extract: 7.93 ml/min.
Flow rate of eluent: 9.22 ml/min.
Step time: 2.5 min.
Concentration of feedstock: 50 mg/ml-mobile phase
Flow rate in zone I: 12.24 ml/min.
Flow rate in zone II: 4.31 ml/min.
Flow rate in zone III: 5.91 ml/min.
Flow rate in zone IV: 3.02 ml/min.

TABLE 2

| Column | Amount of the supported | Conditions of analysis | k1' k2' | Chromatogram |
|---|---|---|---|---|
| W. Ex. 1 | Made in S.E.1 | 24 wt % | (1)* | 1.02 2.57 | FIG. 3 |
| W. Ex. 2 | Made in S.E.2 | 30 wt % | (1)* | 1.73 15.43 | FIG. 4 |
| C. Ex. 1 | Made in S.E.3 | 20 wt % | (1)* | 0.86 2.19 | FIG. 5 |

*The conditions of the analysis in Table 2
(1) Mobile phase: n-hexane/2-propanol/diethylamine 25/72/0.1 (vol.) mixture, Flow rate: 1.0 ml/min., Temperature: 40° C., Detection: 254 nm, Injection amount: 1.5 mg/ml(mobile phase) × 2.5 µl
(2) Mobile phase: 2-propanol/diethylamine 100/0.1 (vol.) mixture, Flow rate: 1.0 ml/min., Temperature: 40° C., Detection: 254 nm, Injection amount: 1.5 mg/ml(mobile phase) × 2.5 µl The values of k1' and k2' were calculated by the following formulae:

$$k1'=(v1-v0)/v0, k2'=(v2-v0)/v0$$

wherein v0 is the retention volume of tri-tert-benzyl benzene, v1 and v2 each are the respective retention volumes of the optical isomers, which are solutes.

TABLE 3

| | W. Ex. 1 | W. Ex. 2 | C. Ex. 1 |
|---|---|---|---|
| Mobile phase | (1) | (1) | (1) |
| Optical purity of raffinate (% ee) | 99.5 | 99.4 | 99.5 |
| Optical purity of extract (% ee) | 94.7 | 94.8 | 94.6 |
| Productivity (kg-rac./kg-CSP/day)* | 3.42 | 3.49 | 3.05 |

The mobile phases in Table 3
(1) n-hexane/2-propanol/diethylamine 25/75/0.1 (vol.) mixture
(2) 2-propanol/diethylamine 100/0.1 (vol.) mixture
*The weight (kg) of a racemic compound that can be separated with 1 kg of the filler per day.

Synthesizing Example 4

Preparation of an HPLC Column Containing a Filler that Includes 30 Weight % of Amylose Tris(3,5-dimethylphenyl carbamate)

(1) Surface Treatment of Silica Gel

The surface treatment was carried out in the same way as explained in Synthesizing Example 1 (1). Then, a carbamoyl-treated silica gel was obtained.

(2) Synthesis of Amylose Tris(3,5-dimethylphenyl carbamate)

Under nitrogen atmosphere, 50 g of amylose and 340.7 g (2.5 equivalent weight) of 3,5-dimethyl isocyanate in 3.8 liters of dried pyridine were heated and stirred for 60 hours at the reflux temperature of pyridine. The solution was poured into 40 liters of methanol. The formed precipitate was isolated by filtration with a glass filter, washed several times with methanol, and then vacuum-dried at 80° C. for 15 hours. The collected was a slightly yellowish white solid product, which weighed 177 g. The yield was 95%.

(3) Preparation of a Filler Made of Silica Gel Supporting 30 Weight % of Amylose Tris (3,5-dimethylphenyl carbamate)

15.0 g of amylose tris(3,5-dimethylphenyl carbamate) obtained in step (2) above was dissolved in 120 ml of ethyl acetate. 35 g of the treated silica gel prepared in step (1) above was uniformly coated with this polymer solution. The ethyl acetate was vacuum-distilled off from the coated silica gel.

Then, the aimed filler made of silica gel supporting 30 weight % of amylose tris(3,5-dimethylphenyl carbamate) was obtained. The carbon content (C %) of this filler determined by elemental analysis and the content of the supported amylose tris(3,5-dimethylphenyl carbamate) in the filler are shown in Table 4.

(4) Preparation of a Filled HPLC Column from the Prepared Filler

A stainless steel column of 25 cm in length and 0.46 cm in inner diameter was filled with the filler made of silica gel supporting amylose tris (3,5-dimethylphenyl carbamate), which was prepared in step (3) above, by the slurry method. Then a separation column for optical isomers was obtained.

Synthesizing Example 5

Preparation of an HPLC Column Containing a Filler that Includes 20 Weight % of Amylose Tris(3,5-dimethylphenyl carbamate)

(1) Surface Treatment of Silica Gel

The surface treatment was carried out in the same way as explained in Synthesizing Example 1 (1). Then, a carbamoyl-treated silica gel was obtained.

(2) Synthesis of Amylose Tris(3,5-dimethylphenyl carbamate)

Amylose tris(3,5-dimethylphenyl carbamate) was synthesized in the same way as explained in Synthesizing Example 4 (2).

(3) Preparation of a Filler Made of Silica Gel Supporting 20 Weight % of Amylose Tris(3,5-dimethylphenyl carbamate)

10.0 g of amylose tris (3,5-dimethylphenyl carbamate) obtained in step (2) above was dissolved in 70 ml of ethyl acetate. 40 g of the treated silica gel prepared in step (1) above was uniformly coated with this polymer solution. The ethyl acetate was vacuum-distilled off from the coated silica gel. Then, the aimed filler made of silica gel supporting 20 weight % of amylose tris(3,5-dimethylphenyl carbamate) was obtained.

(4) Preparation of a Filled HPLC Column from the Prepared Filler

A stainless steel column of 25 cm in length and 0.46 cm in inner diameter was filled with the filler made of silica gel supporting amylose tris (3,5-dimethylphenyl carbamate), which was prepared in step (3) above, by the slurry method. Then a separation column for optical isomers was obtained.

Working Example 3

Measurement of the Capacity Factors and Simulated Moving Bed Chromatographic Separation Using the Column and the Filler Made in Synthesizing Example 4

Warfarin (II) represented by formula (II) was analyzed with the HPLC column made in Synthesizing Example 4, which HPLC column was fixed in a liquid chromatographic apparatus. The conditions of analysis and capacity factors obtained are shown in Table 4.

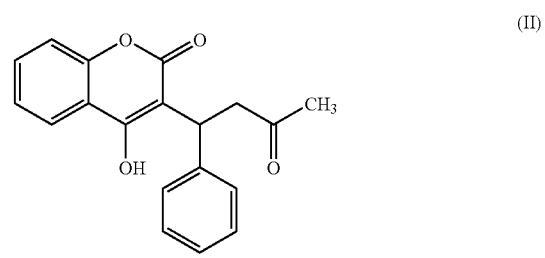

(II)

Eight (8) stainless steel columns, each being 1.0 cm in inner diameter and 10 cm in length, were filled by the slurry method with the filler prepared in Synthesizing Example 4. The columns were fixed to a small-sized simulated moving bed chromatographic separation apparatus and then separation was carried out. The operational conditions are shown below. The respective optical purities of the obtained raffinate and extract, and the productivity of the raffinate are shown in Table 5.

Mobile phase: ethanol/acetic acid 100/0.1 (vol.) mixture
Column temperature: 25° C.
Supply rate of feedstock: 3.15 ml/min.
Flow rate of raffinate: 5.20 ml/min.
Flow rate of extract: 19.20 ml/min.
Flow rate of eluent: 21.25 ml/min.
Step time: 2.5 min.
Concentration of feedstock: 20 mg/ml-mobile phase
Flow rate in zone I: 25.79 ml/min.
Flow rate in zone II: 6.59 ml/min.
Flow rate in zone III: 9.74 ml/min.
Flow rate in zone IV: 4.54 ml/min.

Comparative Example 2

Measurement of the Capacity Factors and Simulated Moving Bed Chromatographic Separation Using the Column and the Filler Made in Synthesizing Example 5

Warfarin (II) represented by formula (II) was analyzed with the HPLC column made in Synthesizing Example 5, which HPLC column was fixed in a liquid chromatographic apparatus. The conditions of the analysis and the capacity factor obtained are shown in Table 4.

Eight (8) stainless steel columns, each being 1.0 cm in inner diameter and 10 cm in length, were filled by the slurry method with the filler prepared in Synthesizing Example 5. The columns were fixed to a small-sized simulated moving bed chromatographic separation apparatus and then separation was carried out. The operational conditions are shown below. The respective optical purities of the obtained raffinate and extract, and the productivity of the raffinate are shown in Table 5.

Mobile phase: ethanol/acetic acid 100/0.1 (vol.) mixture
Column temperature: 25° C.
Supply rate of feedstock: 2.14 ml/min.
Flow rate of raffinate: 4.14 ml/min.
Flow rate of extract: 15.37 ml/min.
Flow rate of eluent: 17.34 ml/min.
Step time: 2.5 min.
Concentration of feedstock: 50 mg/ml-mobile phase
Flow rate in zone I: 21.76 ml/min.
Flow rate in zone II: 6.39 ml/min.
Flow rate in zone III: 8.54 ml/min.
Flow rate in zone IV: 4.42 ml/min.

TABLE 4

Figure 6:
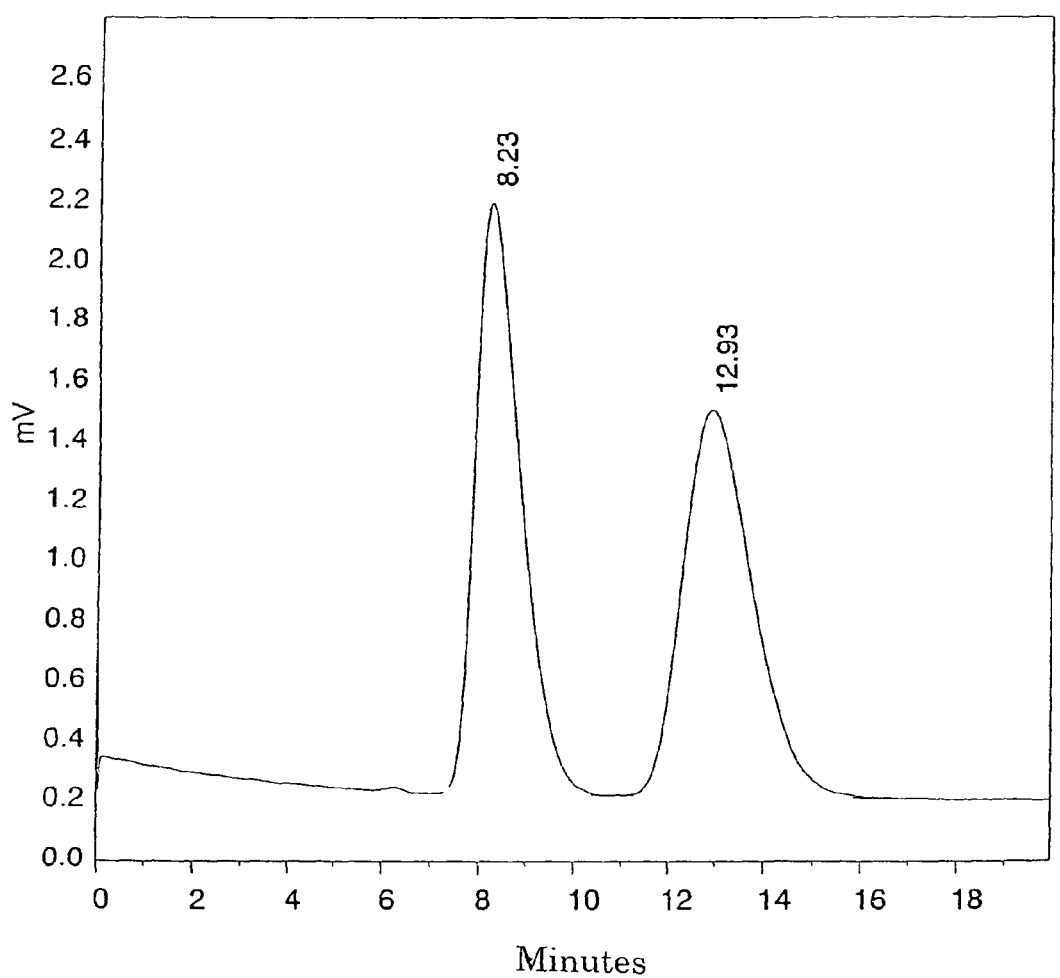
FIG. 6 is a chromatogram obtained in Working Example 3.
Figure 7:
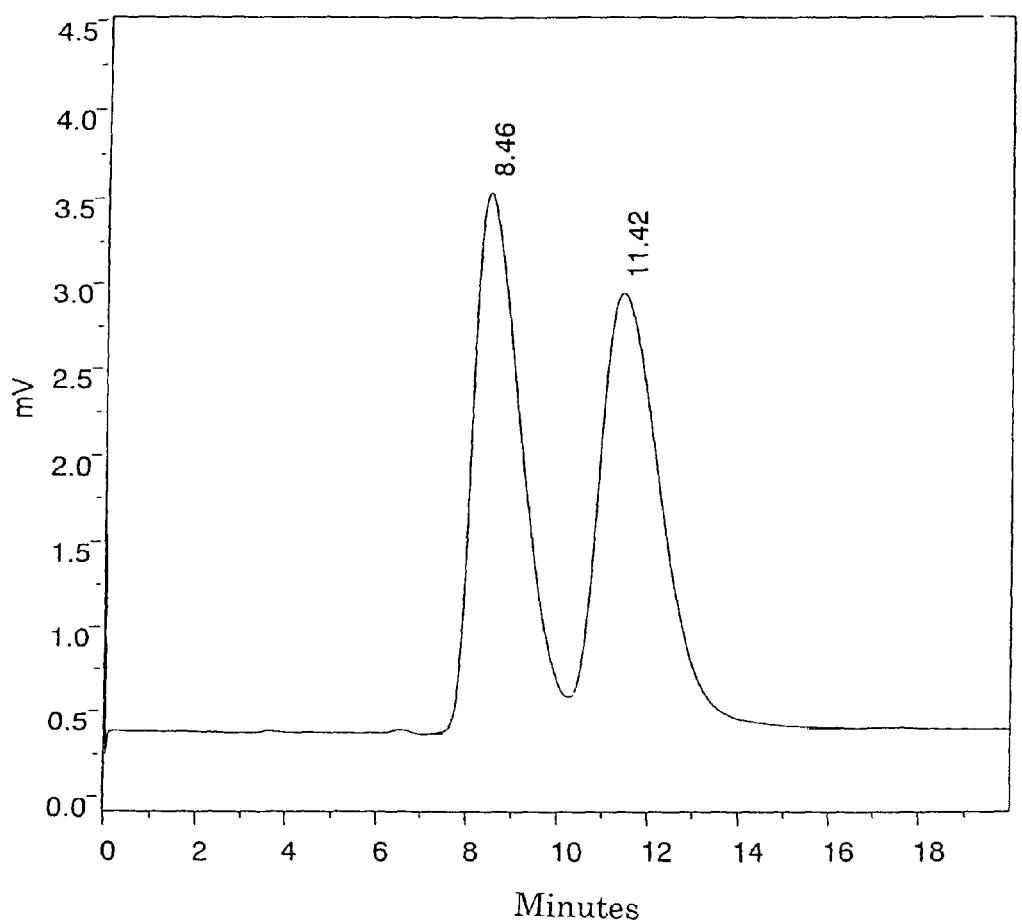
FIG. 7 is a chromatogram obtained in Comparative Example 2.

| Column | | Amount of the supported | Conditions of analysis | k1' k2' | Chromatogram |
|---|---|---|---|---|---|
| W. Ex. 3 | Made in S.E. 4 | 30 wt % | (1)* | 0.43 1.07 | FIG. 6 |
| C. Ex. 2 | Made in S.E. 5 | 20 wt % | (1)* | 0.34 0.74 | FIG. 7 |

*The conditions of the analysis in Table 4 (1) Mobile phase: ethanol/acetic acid 100/0.1 (vol.) mixture, Flow rate: 0.5 ml/min., Temperature: 25° C., Detection: 254 nm, Injection amount: 5.0 mg/ml (mobile phase) × 2.0 μl The definitions of k1' and k2' are the same as those shown above.

TABLE 5

| | W. Ex. 3 | C. Ex. 2 |
|---|---|---|
| Mobile phase | (1) | (1) |
| Optical purity of raffinate (% ee) | 99.7 | 99.6 |
| Optical purity of extract (% ee) | 94.8 | 94.3 |
| Productivity (kg-rac./kg-CSP/day)* | 2.40 | 1.64 |

The mobile phase in Table 5
(1) ethanol/acetic acid 100/0.1 (vol.) mixture
*The weight (kg) of a racemic compound that can be separated with 1 kg of the filler per day.

INDUSTRIAL APPLICABILITY

This invention provides a filler having an excellent optical resolution ability and therefore being suitable for separating optical isomers, with which filler optical resolution can be carried out continuously and efficiently. This invention also provides a process for separating optical isomers by the simulated moving bed chromatography utilizing this filler, which will substantially reduce the industrial production cost.

What is claimed is:

1. A process for separating optical isomers by a simulated moving bed chromatography employing a filler for separating optical isomers, the process including separating the optical isomers with the filler that comprises a carrier and an optically active high molecular weight compound selected from the group consisting of an amylose ester derivative and an amylose carbamate derivative supported on the carrier wherein the amount of the optically active high molecular weight compound supported is at least 23 weight % based on the weight of the filler.

2. The process according to claim 1, wherein the separation is carried out under the condition that at least one of capacity factors k1' and k2' calculated by the following formulae (1) and (2):

$$k1'=(v1-v0)/v0 \quad (1)$$

$$k2'=(v2-v0)/v0 \quad (2)$$

wherein v1 and v2 are the respective retention volumes of the optical isomers, which are solutes, and v0 is a dead volume, has a value of 1 or more.

3. The process according to claim 1, wherein the filler has an average particle size of 5-70 μm.

4. The process according to claim 1, wherein said optically active high molecular weight compound is amylose tris(3,5-dimethylphenylcarbamate).

5. The process according to claim 4, wherein the amount of amylose tris(3,5-dimethylphenylcarbamate) supported is at least 27 weight-% based on the weight of the filler.

6. The process according to claim 4, wherein the amount of amylose tris(3,5-dimethylphenylcarbamate) supported is at least 30 weight-% based on the weight of the filler.

7. The process according to claim 4, the wherein the amount of amylose tris(3,5-dimethylphenylcarbamate) supported is about 30 weight-% based on the weight of the filler.

8. The process according to claim 4, the wherein the amount of amylose tris(3,5-dimethylphenylcarbamate) supported is at least 24 weight-% based on the weight of the filler.

9. The process according to claim 4, the wherein the amount of amylose tris(3,5-dimethylphenylcarbamate) supported is 23-60 weight-% based on the weight of the filler.

* * * * *